US00PP08516P

United States Patent [19]

Winchel

[11] Patent Number: Plant 8,516

[45] Date of Patent: Dec. 28, 1993

[54] HYBRID TEA ROSE PLANT NAMED 'WEKAQ'

[75] Inventor: Joseph Winchel, Harbor City, Calif.

[73] Assignee: Weeks Wholesale Rose Grower, Inc., Upland, Calif.

[21] Appl. No.: 983,462

[22] Filed: Nov. 30, 1992

[51] Int. Cl.[5] ..... A01H 5/00

[52] U.S. Cl. ..... Plt./11

[58] Field of Search ..... Plt./11, 22

*Primary Examiner*—Howard J. Locker

*Attorney, Agent, or Firm*—Christie, Parker & Hale

[57] ABSTRACT

A new variety of Hybrid Tea Rose suitable for garden decoration, having flowers of blended orchid pink colors.

1 Drawing Sheet

BACKGROUND OF THE INVENTION

This invention relates to a new and distinct variety of Hybrid Tea Rose. The varietal denomination of the new variety is 'Wekaq.' The growth habit of the plant is bushy and upright. 'Wekaq' has as its seed parent the variety known as 'Paradise' (U.S. Plant Pat. No. 4,552) and as its pollen parent the variety known as 'Admiral Rodney.'

SUMMARY OF THE INVENTION

Among the features which distinguish the new variety cv. 'Wekaq' from other presently available and known commercial rose cultivars are the following combination of characteristics: unusual blend of orchid pink colors substantially as described and illustrated herein, prolific production of long straight stems, shapely blooms, and attractive upright growth habit with very full branching and abundant foliage. Cv. 'Wekaq' may be propagated by cuttings, budding, grafting and tissue culture.

Asexual reproduction of the new variety by budding as performed in Kern County, Calif. and Upland, Calif. shows that the foregoing and other distinguishing characteristics come true to form and are established and transmitted through succeeding propagation.

Comparison with Parent Varieties

The new rose may be distinguished from its seed parent, 'Paradise,' as follows: whereas 'Paradise' produces flowers of a more lavender blend combination, 'Wekaq' produces flowers of a pink blend coloration substantially as described and illustrated herein; 'Paradise' has a rounded growth habit which is only moderately full branching, whereas 'Wekaq' has a significantly more upright habit with much fuller branching; 'Wekaq' has a dark green foliage with a matte finish, whereas 'Paradise' has significantly darker foliage with a more semi-glossy finish.

The new variety may be distinguished from its pollen parent, 'Admiral Rodney,' as follows: 'Admiral Rodney' is very full-petaled (about 45), whereas 'Wedaq' has significantly fewer petals (24 to 30); 'Wedaq' has a light fragrance, whereas 'Admiral Rodney' has a strong fragrance; whereas the new variety is a very vigorous and productive plant, 'Admiral Rodney' has significantly less vigor and produces fewer flowers.

BRIEF DESCRIPTION OF THE ILLUSTRATION

The accompanying photograph shows the plant and flowers from bud to full bloom depicted in color as nearly correct as it is possible to make in a color illustration of this character. Throughout the description, color values are those set forth in the Colour Chart of The Royal Horticultural Society of London, England, except where common terms of color definition are employed.

DESCRIPTION OF THE NEW VARIETY

The following descriptive matter pertains to roses of the new cultivar grown outdoors in August, 1992 in California. Phenotypic expression may vary with differences in conditions of light, soil and climate.

FLOWER

The new variety usually bears its flowers singly, sometimes in flat to rounded clusters of two to three blooms per stem. Flowers are borne on normally strong stems of medium length for the class. Outdoors, the plant blooms very abundantly and nearly continuously during the growing season. The flowers have a slight tea fragrance.

BUD

The peduncle is average to moderately long for the class, of average to heavy caliper, and usually erect. It is moderately smooth with some stipitate glands and hairs. Peduncle color is between 144A and 138A, often blushed on the side facing the sun with near 183B.

Before the calyx breaks, the bud is of medium size for the class, moderately long in length, and pointed to ovoid in shape. The surface of the bud bears several stipitate glands, usually with slender foliaceous parts extending beyond the tip of the bud equal to about one-half or more of its length. Bud color is between 144A and 138A, oftern blushed on the side facing the sun with near 183B.

The inner surface of the sepals is covered with fine woolly tomentum; sepal margins are lined with some stipitate glands and hairs.

As the first petals open, the bud is of medium size for the class, medium to long in length, and very pointed to ovoid in form. The color of the outside surfaces of the newly opened petals is between 57C and 60B with a small basal attachment coloration of near 2C. The color of the inside surfaces of the newly opened petals is between 62B and 62D, deepening toward the petal edge to as deep as between 57C and 60D with a medium-sized basal attachment coloration of near 3C. The bud opens well and is not prevented from opening by cold, hot or dry weather.

BLOOM

When fully open, the bloom is medium to moderately large for the class, ranging from 10 to 13 cm. in diameter. Petalage is double with 24 to 30 petals and 5 to 8 or more petaloids arranged regularly. When partially open, the bloom form is very high-centered and the petals are moderately cupped to undulated with petal edges somewhat rolled under. When fully open, the bloom form is more cupped to full, and the petals are more undulated with petal edges undulated and less rolled under.

PETALS

The petals are somewhat heavy in substance and moderately thick with inside surfaces somewhat satiny to shiny and outside surfaces only slightly satiny. The outer petals are very broadly round to slightly obovate in shape with apices mostly rounded to occasionally slightly mucronate. The inner petals are more broadly obovate in shape with apices mostly rounded.

NEWLY OPENED FLOWER

The outside surface of the outer petals is between 62B and 63C, deepening toward the petal edge to as deep as between 57C and 60D and with a small basal attachment zone with coloration of near 2C. The inside surface of the outer petals is between 62D and 62C, deepening toward the petal edge to as deep as between 57C and 60D and with a medium-sized basal attachment zone with coloration of near 3C.

The outside and inside surface of the intermediate petals is as above with a more narrow zone of darker coloration toward the edge of the petals.

The outside and inside surface of the inner petals is as above with almost no darkening toward the edge of the petals.

The general tonality of the newly opened flower is between 62D and 62C, with the outer petal edges deepening to as deep as between 57C and 60D.

THREE-DAY-OLD FLOWER

The outside surface of the outer petals is between 62C and 65B, deepening toward the petal edge to as deep as betwen 61C and 63B and with a medium-sized basal attachment zone with coloration of near 155A. The inside surface of the outer petals is between 62D and 65C, deepening toward the petal edge to as deep as between 61C and 63B and with a broad basal attachment zone with coloration of near 158C.

The outside surface of the inner petals is as above with very little to none of the darkening toward the edge of the petals.

The general tonality of the three-day-old flower is between 62D and 65C, with the outer petal edges deepening to as deep as between 61C and 63B.

On the spent bloom, the petals usually drop off cleanly but sometimes persist, fading mostly to between 65D and 56D.

In August, blooms on the bush growing outdoors generally last from three to four or more days. Cut roses grown outdoors and kept at normal room temperatures generally last from four to five or more days.

REPRODUCTIVE ORGANS

Stamens are average in number and are irregularly disposed about the pistil; a few are mixed with petaloids or trucked in the calyx. The filaments are of irregular length, most with anthers. The anthers are somewhat small to medium for the class and all open approximately at the same time. Anther color is near 22B when immature and near 165A at maturity. Pollen is somewhat sparse and near 20D in color.

Pistils are average in number (approximately 80). The styles are very uneven, moderately short to average in length, somewhat thin to average in caliper, and moderately bunched together. Stigma color is near 14D. Style color is near 45C. Ovaries are usually enclosed in the calyx, although some may protrude from the calyx as vegetative growth under the conditions of cool night temperatures.

Hips have not been observed on this variety when grown in Upland, Calif. as 'Wekaq' appears to be nearly female-sterile.

FOLIAGE

The compound leaves are usually comprised of three to five leaflets and are borne very abundantly. The leaves are moderately sized for the class, somewhat heavy to leathery in texture, and mostly matte in finish. The leaflets are shaped very oval with somewhat acute to mucronate apices and moderately round to acute bases. Their margins are usually irregularly serrate.

The upper surface of the mature leaf is between 147A and 139A. The under surface of the mature leaf is between 147C and 138C, usually very lightly suffused with near 184C. The upper and under surface of the young leaf is between 147A and 139A, usually heavily suffused with near 183B.

The rachis is moderately light to average in caliper and very grooved with some hairs and stipitate glands. The under side of the rachis is somewhat rough with some hairs and stipitate glands and a few prickles.

The stipules are of medium length with somewhat narrow to medium width and length and straight points that usually turn out an an angle of less than 45 degrees.

The plant displays an average degree of resistance to powdery mildew and blackspot as compared to other commercial varieties grown under comparable conditions in Upland, Calif.

GROWTH

The plant growth habit is bushy, upright and of medium height with very full branching. It displays very vigorous growth and the canes are of medium to heavy caliper for the class.

The color of the major stems is between 152C and 146C. They bear some large prickles which are of moderately short length for the class. The large prickels are almost straight, hooked slightly downward, with a short to medium length and broad base; prickle color is near 165C. The major stems bear no small prickles and no hairs.

The color of the branches is between 146B and 138A. They bear some large prickles which are moderately short for the class. The large prickles are almost straight, hooked slightly downward, with a short to medium length, and broad base; prickle color is near 163C. The branches bear a few small prickles of the same coloration. There are no haris.

The color of the new shoots is between 146B and 138A, usually heavily suffused with near 183B. They bear several large prickles which are moderately short for the class. The large prickles are almost straight but hooked slightly downward, with a short to medium length and broad base; prickle color is near 184C. The shoots bear some small prickles of the same coloration. There are no hairs.

I claim:

1. A new and distinct variety of Hybrid Tea Rose plant substantially as described and illustrated herein.

* * * * *

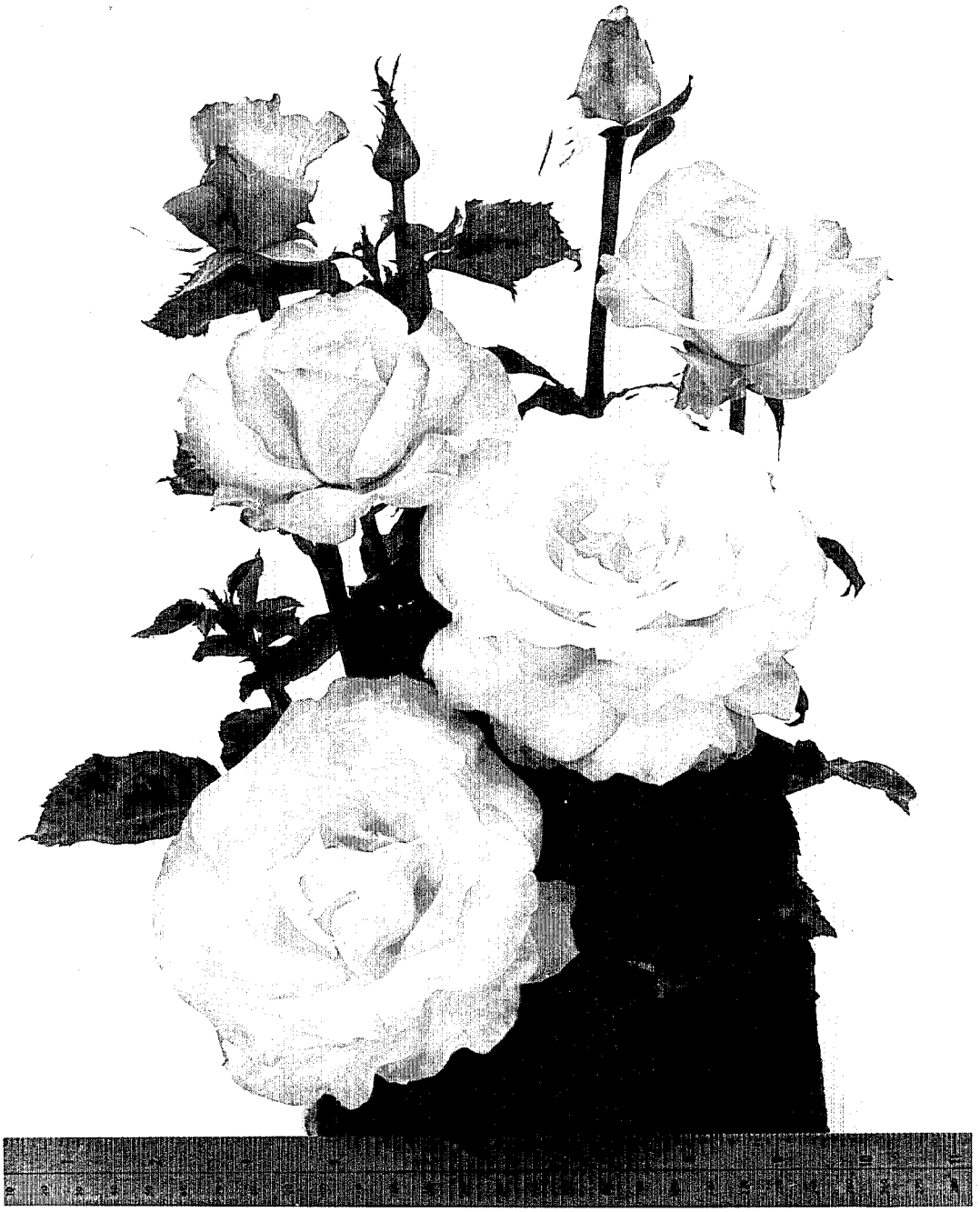

UNITED STATES PATENT AND TRADEMARK OFFICE

CERTIFICATE OF CORRECTION

PATENT NO. : Plant 8,516

DATED : December 28, 1993

INVENTOR(S) : Joseph Winchel

It is certified that error appears in the above-indentified patent and that said Letters Patent is hereby corrected as shown below:

Column 2, line 40, change "oftern" to -- often --.

Column 3, line 50, change "betwen" to -- between --.

Column 4, line 5, change "trucked" to -- tucked --.
Column 4, line 44, after "turn out" change "an" to -- at --.
Column 4, line 57, change "prickels" to -- prickles --.
Column 4, line 68, change "haris" to -- hairs --.

Signed and Sealed this

Eleventh Day of October, 1994

*Attest:*

*Attesting Officer*

BRUCE LEHMAN

*Commissioner of Patents and Trademarks*